(12) United States Patent
Czarske et al.

(10) Patent No.: US 10,520,594 B2
(45) Date of Patent: Dec. 31, 2019

(54) METHOD AND FIBRE-OPTICAL SYSTEM FOR ILLUMINATING AND DETECTING AN OBJECT BY MEANS OF LIGHT (71) Applicant: TECHNISCHE UNIVERSITÄT DRESDEN, Dresden (DE)

(72) Inventors: Jürgen Czarske, Dresden (DE); Robert Kuschmierz, Dresden (DE)

(73) Assignee: TECHNISCHE UNIVERSITAT DRESDEN, Dresden (DE)

( * ) Notice: Subject to any disclaimer, the term of this patent is extended or adjusted under 35 U.S.C. 154(b) by 0 days.

(21) Appl. No.: 16/232,201

(22) Filed: Dec. 26, 2018

(65) Prior Publication Data

US 2019/0227152 A1 Jul. 25, 2019

(30) Foreign Application Priority Data

Jan. 24, 2018 (EP) .................................. 18153149

(51) Int. Cl.
*G02B 6/04* (2006.01)
*G02B 23/24* (2006.01)
(Continued)

(52) U.S. Cl.
CPC ............ *G01S 7/497* (2013.01); *G01S 7/4818* (2013.01); *G01S 17/026* (2013.01); *G02B 6/04* (2013.01); *G02B 23/2469* (2013.01)

(58) Field of Classification Search
CPC ...... G01S 7/497; G01S 7/4818; G01S 17/026; G02B 23/24; G02B 23/2407; G02B 23/2469; G02B 23/26; G02B 6/04; G02B 6/06
See application file for complete search history.

(56) References Cited

U.S. PATENT DOCUMENTS 7,801,405 B2 * 9/2010 Daum .................. G06T 3/4053
   385/115
8,585,587 B2 * 11/2013 French ............... A61B 1/00165
   600/178
(Continued)

FOREIGN PATENT DOCUMENTS

DE        60223130 T2    8/2008
WO      2004032386 A1    4/2004
(Continued)

OTHER PUBLICATIONS

Kim et al., "Toward a Miniature Endomicroscope: Pixelation-free and Diffraction-Limited Imaging Through a Fiber Bundle," Optical Society of America, vol. 39, No. 7, Apr. 1, 2014, pp. 1921-1924.
(Continued)

*Primary Examiner* — John Bedtelyon
(74) *Attorney, Agent, or Firm* — Heslin Rothenberg Farley & Mesiti P.C.

(57) ABSTRACT

A method and a fibre-optical system for illuminating and detecting an object by light includes in situ calibration of a fibre bundle and disturbance-corrected illumination or disturbance-corrected detection of an object, in particular for endoscopic and microscopic applications, and makes it possible to directly determine the single phase distortion of the light, caused by the transmission by the fibre bundle, in order to calibrate the fibre bundle, and thus provides a possibility for determining the system function of a fibre bundle that is improved compared with the prior art of measuring the double phase distortion. The system function is used for disturbance correction when illuminating or detecting the object.

19 Claims, 2 Drawing Sheets

(51) Int. Cl.
G01S 7/497 (2006.01)
G01S 7/481 (2006.01)
G01S 17/02 (2006.01)

(56) References Cited

U.S. PATENT DOCUMENTS

| | | | |
|---|---|---|---|
| 9,470,883 B2* | 10/2016 | Kalkbrenner | G02B 21/0032 |
| 9,632,296 B2* | 4/2017 | Wolleschensky | G02B 21/002 |
| 9,864,182 B2* | 1/2018 | Kleppe | G02B 21/16 |
| 10,281,701 B2* | 5/2019 | Kleppe | G02B 21/0064 |
| 2015/0015879 A1 | 1/2015 | Papadopoulos et al. | |
| 2015/0370012 A1* | 12/2015 | Ishihara | G02B 6/06 348/308 |
| 2017/0285324 A1* | 10/2017 | Hua | G02B 23/2469 |

FOREIGN PATENT DOCUMENTS

| | | |
|---|---|---|
| WO | 2010004297 A1 | 1/2010 |
| WO | 2017174596 A1 | 10/2017 |

OTHER PUBLICATIONS

Kim et al., "Transmission Matrix of a Scattering Medium and Its Applications in Biophotonics," Optical Society of America, vol. 23, No. 10, May 18, 2015, 22 pp.

Mahalati et al., "Resolution Limits for Imaging Through Multi-Mode Fiber," Optical Society of America, vol. 21, No. 1, Jan. 14, 2013, pp. 1656-1668.

Conkey et al., "Lensless Two-Photon Imaging Through a Multicore Fiber with Coherence-Gated Digital Phase Conjugation," Journal of Biomedical Optics, vol. 21, No. 4, Apr. 2016, 045002-1-045002-9.

Extended European Search Report for International Patent Application No. EP 18153149.2, dated Sep. 12, 2018.

Meng Cui, "Implementation of a digital optical phase conjugation system and its application to study the robustness of turbidity suppression by phase conjugation," Optics Express 18, vol. 4 (2010), pp. 3444-3455.

Ruo Yu Gu, "Design of flexible multi-mode fiber endoscope," Optics Express 23, vol. 21 (2015) pp. 26905-26918.

* cited by examiner

METHOD AND FIBRE-OPTICAL SYSTEM FOR ILLUMINATING AND DETECTING AN OBJECT BY MEANS OF LIGHT

CROSS REFERENCE TO RELATED APPLICATIONS

This U.S. application claims priority to European Application No. 18153149.2, filed on Jan. 24, 2018, the entire contents of which are incorporated herein by reference.

BACKGROUND ART

The invention relates to a method and a fibre-optical system for illuminating and detecting an object by means of light, in particular for endoscopic and microscopic applications. The invention comprises in situ calibration of fibre-optical image waveguides (fibre bundles) and disturbance correction of illumination or detection.

Fibre-optical systems in the form of flexible endoscopes comprise a high number (up to several 100,000) of individual, flexible optical fibres, e.g. glass fibres. If the individual fibres of a fibre bundle are arranged coherently, optical image transmission can be carried out. Advantages compared with rigid endoscopes, in which the image information is transferred via a rod lens system, are in particular the compactness of the extremely fine fibre bundle and the flexible use possibilities, even when access to the observed object is extremely restricted. A disadvantage of flexible endoscopes is that the achievable image contrast is relatively low. This is caused in particular by the pixelation of the fibre bundle, the crosstalk between the individual fibres, leading to a reduction in the image sharpness (blur effect), and multi-mode nature of the light wave guidance in the individual fibres (speckle effect). The deterioration in the image quality owing to the described disturbances from the fibre bundle can be described by means of a modulation transfer function. Furthermore, flexible fibre bundles only allow for transmission of intensity profiles and the imaging thereof using lenses (near-field technology). Owing to the different and unknown optical path lengths of the individual fibre, the phase information of the transmitted light is not directly accessible, and therefore the far field of the transmitted light is unknown and cannot be specifically adjusted.

A reduction in the pixel spacing of an image made using a flexible endoscope can be achieved by integrating imaging optics, generally an optical lens or a lens system which images the distal plane of the fibre bundle onto the object plane. However, this significantly increases the installation size of the endoscope, and therefore the minimum dimension for optical access is increased. Moreover, complex construction and connection techniques are required for integrating the imaging optics, as well as numerous adjustment steps. A further disadvantage results from the fact that fibre bundles comprising conventional imaging optics allow for only two-dimensional measurements in the lateral plane. In order to obtain depth information, for example scanning methods have to be carried out using mechanically displaceable optical elements or electrically adjustable optics, or other complex measurement methods (triangulation using two fibre bundles).

Various approaches exist for correcting disturbances caused by transmission through optical waveguides. WO 2004/032386 A1 describes a method for correcting polarisation-dependent disturbances in light waveguides, a compensation function for the polarisation-dependent disturbances being calculated by the light waveguide, by means of which function a distorted electrical input signal is first calculated, which signal is converted into a corresponding distorted optical input signal which is intended to be transmitted via the light waveguide. In order to determine the compensation function, a detector is used which is configured for measuring the signal-noise ratio, the polarisation-dependent attenuation or mode dispersion, the bit error rate, or the signal dispersion.

Adaptive optics methods are known from the prior art, in which phase aberrations can be detected and equalised by using wavefront sensors and modulators. Methods of this kind for beam control of high-energy laser beams are disclosed for example in DE 602 23 130 T2. Cui, M. and Yang, C. *Implementation of a digital optical phase conjugation system and its application to study the robustness of turbidity suppression by phase conjugation*. Optics Express 18, Vol. 4 (2010), page 3444 proposes an adaptive optics method comprising an open control loop that is referred to as "digital optical phase conjugation" and is suitable for correcting phase distortions through an optically opaque, in particular biological, medium. In this case, a CCD camera is used as a sensor and a spatial light modulator (SLM) is used as an actuator. The described method requires each pixel of the camera to generate a virtual image on a corresponding pixel of the SLM, and vice versa. As a result, the method requires complex calibration and a very high degree of adjustment work. Gu, R. Y., Mahalati, R. N. and Kahn, J. M. *Design of flexible multi-mode fiber endoscope*. Optics Express 23, Vol. 21 (2015), page 26905 describes an endoscope comprising flexible multi-mode fibres which can be calibrated using a partial reflector at the distal end and an SLM at the proximal end. Calibration of the endoscope and measurements using the endoscope cannot be carried out simultaneously. The specifications "proximal" and "distal" characterise positional relationships with respect to the fibre bundle, the proximal side of the fibre bundle being the end face that faces the illumination source, and the distal side of the fibre bundle being the end face that faces the object.

U.S. Pat. No. 8,585,587 B2 described a flexible endoscope in which the relative phase of the incident light can be changed using an SLM arranged at the proximal fibre end. The phase difference caused by the fibres with respect to the incident light is determined by means of a wavefront sensor or interferometer. For this purpose, a partially reflective coating is applied to the distal fibre ends. As a result, the phase difference $\Delta\phi$ is determined after the light has passed through the fibre bundle twice, and therefore it is not the single phase difference that is measured but instead $2\Delta\phi$, modulo $2\pi$ in each case. The disadvantage of measuring the double phase difference is that this measurement is unclear. For example, if a double phase difference about $\pi$ is measured, the single phase difference caused by the fibre bundle may be $\pi/2$ or $-\pi/2$. The true single phase difference can be determined only using complex methods.

In order to overcome this, US 2015/0015879 A1 proposes distally illuminating a multi-mode waveguide by means of a virtual light source image. A multi-mode fibre that has a double sheathing and comprises a single-mode fibre core is considered, at the distal end of which fibre a holographic photographic material and a point-reflection generating object (by which a virtual light source is generated behind the object) are positioned. In the event of illumination, the wave transmitted by the single-mode fibre interferes constructively, at the location of the photographic material, with the light emanating from the virtual light source. It is disadvantageous that the position of the virtual light source is fixed and cannot be freely selected, and therefore the position selection for the real focus is also greatly restricted. Moreover, a specific optical design is necessary at the distal fibre end.

BRIEF SUMMARY OF THE INVENTION

The object of the present invention is therefore that of proposing an improved method and an associated fibre-optical system, by means of which the disturbances caused by transmitting the light emitted by an illumination source through a bundle of optical fibres can be corrected, without it being necessary to repeatedly carry out complex adjustment steps in order to calibrate the system. In other words, the bundle of optical fibres is intended to be able to be used as a coherent phase array ("remote phased array") for light.

The method according to the invention for illuminating and detecting an object by means of light comprises calibration of a coherent bundle of optical fibres and disturbance-corrected illumination or disturbance-corrected detection of the object. The coherent bundle of optical fibres, for example glass fibres, is in particular flexible. The calibration in method step a) is used at least for identifying and evaluating the system function of the fibre bundle, which can be shown by the transmission matrix between the proximal and the distal end of the fibre bundle and is also sometimes referred to in literature as the "transmission function". In method step b), the determined disturbance is largely compensated for when observing the object. The disturbance may be visualised for example as distortion of the wavefronts of the light or as deformation of the wave field. Observation of the object comprises the illumination and detection thereof.

By means of the method according to the invention, the calibration of the fibre bundle and the disturbance-compensated observation of the object can advantageously be carried out in situ, such that changes in the system function, for example caused by movement, vibration or temperature changes, can be immediately identified, without complex manual adjustment.

An ordered fibre bundle is referred to as "coherent" if the positional relationship between two fibres of the bundle in each case remains constant over the entire length of the bundle. Positional relationships with respect to the fibre bundle are frequently characterised, in the following, by the specifications "proximal" and "distal", the proximal side of the fibre bundle being the end face that faces the illumination system, and the distal side of the fibre bundle being the end face that faces the object.

The method according to the invention comprises the following sub-method steps for calibrating the fibre bundle in method step a):

i) proximal illumination of at least one freely selectable individual fibre of the coherent bundle optical fibre with light;
ii) reflecting the light at least in part at means for partial reflection of the light that are spaced apart from the distal facets of the optical fibres of the bundle, such that a region of the bundle of optical fibres that comprises more than one individual fibre is illuminated distally by the reflected light, the reflected light corresponding to the light emanating from the virtual image of the illuminated individual fibres;
iii) detecting the spatial intensity distribution of the reflected light subjected to disturbance by being transmitted by means of the distally illuminated region of the bundle of optical fibres, or the spatial intensity distribution of an interference pattern generated by coherently superposing a reference wave on the reflected light subjected to disturbance by being transmitted by means of the distally illuminated region of the bundle of optical fibres;
iv) evaluating the detected data at least in order to directly extract the single phase difference $\Delta\Phi$ of the reflected light subjected to disturbance by being transmitted by means of the distally illuminated region of the bundle of optical fibres;
v) determining a system function that mirrors the transmission properties of the distally illuminated region of the bundle of optical fibres;
vi) repeating method steps i) to v) in order to determine a system function that mirrors the transmission properties of the entire bundle of optical fibres.

For calibrating the fibre bundle, use is made of the fact that, when the light guided through an individual fibre of the fibre bundle is reflected at the means for partial reflection on the face of the means for partial reflection that does not face the fibre bundle, a virtual image of the individual fibres results on the distal face of the fibre bundle, it being possible to consider the reflected light to be emerging from said approximately punctiform virtual source. Illumination thus occurs distally, from the virtual light source, the number of distally illuminated fibres of the fibre bundle being dependent on the spacing between the virtual light source and the distal facets of the fibre bundle. The use of the approximately punctiform virtual light source is analogous to the guide star concept, known from astronomy, and therefore the approximately punctiform virtual light source is also referred to in the following as a "guide star".

In sub-method step iii), the spatial intensity distribution of the reflected light, i.e. the light that is subjected to disturbance by being transmitted by means of the region of the fibre bundle that is illuminated distally by the virtual light source is detected, or an interference pattern that is generated by coherently superposing a reference wave on the reflected light, i.e. the light subjected to disturbance by being transmitted by means of the distally illuminated region of the fibre bundle, is detected; In this case, according to the invention, owing to the distal illumination of the fibres by means of the guide star, the detected data allow for extraction of the single phase difference $\Delta\Phi$ instead of the double phase difference $2 \cdot \Delta\Phi$ as is the case in the event of purely proximal illumination.

It is possible, in principle, to proximally illuminate a single fibre of the fibre bundle and to arrange the means for partial reflection sufficiently far from the distal facets of the fibre bundle that the guide star arises at a sufficiently large distance from the distal facets of the fibre bundle to illuminate the entire fibre bundle. Sub-method step vi) can then be omitted, since a system function that mirrors the transmission properties of the entire bundle of optical fibres has already been determined by means of sub-method steps i) to v). However, a large spacing between the means for partial reflection and the distal facets of the fibre bundle may lead to imaging errors and negatively influence the quality of the calibration. The method according to the invention is therefore advantageously applied such that the spacing between the means for partial reflection and the distal facets of the fibre bundle is selected such that just one portion of the fibre bundle around the proximally illuminated individual fibres is illuminated distally. Sub-method steps i) to v) can be repeated until a system function that mirrors the transmission properties of the entire bundle of optical fibres has been determined. For this purpose, in sub-method step i) individual fibres that are different from one another in each case are illuminated proximally, such that different portions of the fibre bundle are illuminated distally, each portion being captured at least once and the system function of the entire bundle being calculated by combining the system functions of the portions. The spacing between the means for partial reflection and the distal facets of the fibre bundle may typically be approximately 100 µm.

Generating a plurality of guide stars provides the advantage of more precise calibration at a good focal quality. In order to advantageously reduce the duration of the calibration, in an embodiment of the method according to the invention sub-method step i) is implemented such that at least two non-adjacent individual fibres of the bundle of optical fibres are proximally illuminated at the same time, at least two virtual images of the individual fibres resulting in sub-method step ii), by means of which images non-overlapping regions of the fibre bundle are illuminated distally.

For the purpose of observing the object, the method according to the invention comprises the following method step b):

b) disturbance-corrected proximal illumination of the entire bundle of optical fibres by means of light, and detection of the object arranged in the optical path after the means for partial reflection, or disturbance-corrected detection of the object arranged in the optical path after the means for partial reflection following uncorrected proximal illumination of the entire bundle of optical fibres by means of light, the disturbance correction of the illumination being carried out in that the inverse of the system function is impressed on the light emitted by an illumination system, by means of interaction with a wavefront modulator comprising individually actuatable elements, such that, following transfer through the bundle of optical fibres, a wave field that largely corresponds to that emitted by the illumination system is available for proximal illumination of an object arranged in the optical path after the means for partial reflection;

the disturbance correction of the detection being carried out in that the spatial intensity distribution of the light subjected to disturbance by being transmitted by means of the bundle of optical fibres, following interaction with the object, or the spatial intensity distribution of an interference pattern generated by coherently superposing a reference wave on the light subjected to disturbance by being transmitted by means of the bundle of optical fibres, following interaction with the object, is numerically corrected by means of applying the inverse system function.

After the calibration of the fibre bundle has been carried out in method step a), by means of which calibration the system function that mirrors the transmission properties of the entire fibre bundle is determined, the disturbance correction can be carried out before the object is illuminated by the fibre bundle or after the object is illuminated by the fibre bundle.

Thus, in order to compensate for the disturbance caused during transmission of the light through the fibre bundle, the object is either illuminated by a wavefront that is pre-distorted by a wavefront modulator in accordance with the inverse system function, or the illumination is carried out using a wavefront that is not pre-distorted, the distortion of which by the fibre bundle is compensated for numerically after dispersion at the object. Within the meaning of this invention, a "wavefront modulator" is intended to be understood as a device for influencing the phase and/or the amplitude of a light wave in a deliberate manner.

In an embodiment of the method according to the invention, in sub-method step i) at least one freely selectable individual fibre is illuminated proximally by means of at least one first illumination source, and in method step b) the disturbance-corrected or uncorrected proximal illumination of the entire coherent bundle of optical fibres is carried out by means of a second illumination source or, in sub-method step i) the proximal illumination of at least one freely selectable individual fibre and in method step b) the disturbance-corrected or uncorrected proximal illumination of the entire bundle of optical fibre are carried out using exactly one illumination source, the light interacting with a wavefront modulator that is arranged in the optical path between the illumination source and the coherent bundle of optical fibres, at least for the purpose of proximal illumination of at least one freely selectable individual fibre. In this case, the individually actuatable elements of the wavefront modulator are oriented such that the main portion of the light of the illumination source does not strike the fibre bundle but instead only the portion used for illuminating at least one individual fibre, it also being particularly advantageously possible, according to the embodiment described above, to illuminate a plurality of non-adjacent individual fibres at the same time.

The frequency at which the calibration of the fibre bundle is to be carried out is generally determined by the characteristic time scale of the disturbance caused by the fibre bundle, because the system function in method step a) and method step b) should be at least substantially identical. In this case, method step a) and method step b) can be carried out in any desired sequence, e.g. a)-b)-a)-b) or a)-b)-b)-b)-a)-b)-b)-b). Embodiments of the invention are also suitable for carrying out method step a) and method step b) simultaneously, in particular if the disturbance correction of the detection is carried out numerically.

According to an embodiment of the method according to the invention the light is largely reflected or largely transmitted on the distal side of the bundle of optical fibres, depending on the wavelength thereof. This design advantageously makes it possible for the fibre bundle to be calibrated and for an object to be observed by means of the fibre bundle at the same time, in that light of one wavelength, which is largely reflected at the distal end of the fibre bundle, is used for the calibration, and light of another wavelength, which is largely transmitted at the distal end of the fibre bundle, is used for observing the object. This procedure allows for clean separation of detected signals with respect to the optical path thereon, on the basis of the wavelength.

According to a further embodiment of the method according to the invention the light is largely reflected or largely transmitted on the distal side of the bundle of optical fibres, depending on the polarisation state thereof. This design advantageously makes it possible for the fibre bundle to be calibrated and for an object to be observed by means of the fibre bundle at the same time, in that light of one polarisation state, which is largely reflected at the distal end of the fibre bundle, is used for the calibration, and light of another polarisation state, which is largely transmitted at the distal end of the fibre bundle, is used for observing the object. This procedure allows for clean separation of detected signals with respect to the optical path thereon, on the basis of the polarisation state.

A further embodiment of the method according to the invention is characterised in that the evaluation of the detected data and the extraction at least of the phase information of the reflected light subjected to disturbance by being transmitted by means of the distally illuminated region of the fibre bundle is carried out by means of digital holography. In this case, the spatial intensity distribution of an interference pattern resulting from coherently superposing a reference wave on the reflected, disturbed light is detected and evaluated. The reference wave is particularly preferably generated by means of beam splitting of the light emitted by the illumination system. The digital holography advantageously provides the possibility of determining the phase information quickly and without complex iterations. The frequency of the disturbance correction is substantially limited by the assembly, for example by the frequency at which the elements of the wavefront modulator can be adjusted.

In a further embodiment of the method according to the invention, the evaluation of the detected data and the extraction, from the detected intensity distribution, at least of the phase information of the reflected light subjected to disturbance by being transmitted by means of the distally illuminated region of the fibre bundle is carried out by means of numerical reconstruction using a phase-retrieval method. For example, the transport of intensity equation may be evaluated, it being necessary for this purpose for the intensity distribution to be detected at at least two different points along the optical path.

In a further embodiment, the method according to the invention is broadened in that a light pattern that can be freely adjusted over a wide parameter range, in particular also comprising a plurality of focal points, is generated on the distal side of the fibre bundle. For this purpose, the individually actuatable elements of a proximal wavefront modulator are actuated accordingly. The disturbance compensation of the illumination can also be carried out simultaneously by means thereof. Depth information regarding an observed object can advantageously be obtained due to the possibility of focussing using the wavefront modulator. Scans can be carried out, and the method can be used for actuator-like applications of light, e.g. for optical tweezers or radiation therapy.

In addition to the described method, the invention also relates to an associated fibre-optical system.

The fibre-optical system according to the invention for illuminating and detecting an object by means of light comprises an illumination system by means of which a coherent bundle of optical fibres, for example glass fibres, is illuminated, the fibre bundle in particular being flexible.

Means for partial reflection of the light emitted by the illumination system are arranged in the optical path between the distal facets, i.e. the end faces of the fibres of the fibre bundle facing the object and remote from the illumination system, and the object to be observed. The means for partial reflection are spaced apart from the distal facets, i.e. not directly adjacent to the distal facets (for example not deposited thereon).

Furthermore, the fibre-optical system according to the invention comprises means for detecting the spatial intensity distribution of the light that is subjected to disturbance by being transmitted by means of the fibre bundle, or for detecting an interference pattern that is generated by coherently superposing a reference wave on the light subjected to disturbance by being transmitted by means of the bundle of optical fibres. The disturbance may be visualised for example as distortion of the wavefronts of the light or as deformation of the wave field.

Moreover, the fibre-optical system according to the invention comprises a signal processing platform at least for evaluating the detected data and for determining at least the phase information of the light that is subjected to disturbance by being transmitted by means of the fibre bundle.

In addition to the components mentioned, the system according to the invention may also comprise further optical components, in particular beam splitters, that are arranged in an expedient manner.

According to the invention, the illumination system is designed both to illuminate at least one freely selectable individual fibre of the bundle of optical fibres in order to calibrate the fibre-optical system, and to illuminate the entire bundle of optical fibres in order to detect the object. In this case, the calibration of the fibre-optical system comprises at least identifying and evaluating the system function of the fibre bundle, which can be shown in particular by the transmission matrix between the proximal and the distal end of the fibre bundle.

By means of the fibre-optical system according to the invention, both its calibration, and the detection and observation of the object can advantageously be carried out in situ and instantly, such that changes in the system function, for example caused by movement, vibration or temperature change, can be immediately identified, without complex manual adjustment.

As already set out in the description of the method according to the invention, the solution according to the invention is based substantially on directly measuring the single phase difference $\Delta\phi$ when the light emitted by the illumination system passes through, in order to calibrate the fibre-optical system, and using the system function thus determined in order to correct disturbances when observing the object, in that either the inverse of the system function is applied to the proximal illumination of the entire fibre bundle, or the inverse of the system function is used for numerical correction of the measurement data characterising the object.

The fibre-optical system according to the invention can advantageously be used for creating images, the lateral resolution of which is no longer limited by the pixel spacing of the fibre bundle (usually >3.3 µm), but instead only by the numerical aperture of the light-guiding fibre cores. In this case, depending on the diameter of the fibre cores, a lateral resolution of less than 1 µm can be achieved.

The fibre-optical system according to the invention preferably comprises instruments only on the proximal side of the fibre bundle. No active or enlarging optical elements are required at the distal end of the fibre bundle. It is thus advantageously possible to produce ultrathin endoscopes by means of the invention, the diameter of which endoscopes on the distal side is substantially determined by the diameter of the fibre bundle.

In an embodiment of the fibre-optical system according to the invention, the illumination system comprises at least one illumination source and a wavefront modulator that comprises a plurality of individually actuatable elements, the wavefront modulator being arranged in the optical path between the proximal facets of the optical fibres of the bundle and the at least one illumination source. The elements of the wavefront modulator can be oriented such that at least one freely selectable individual fibre of the bundle of optical fibres is illuminated proximally by the at least one illumination source in order to calibrate the fibre-optical system. The portion of the illumination light that is not required for illuminating the at least one individual fibre is deflected by the wavefront modulator such that it does not strike the fibre bundle. Within the meaning of the invention, "at least one individual fibre" means that it is also possible for a plurality of non-adjacent individual fibres of the fibre bundle to be proximally illuminated at the same time or in succession for the purpose of calibration; it does not mean that a region around an individual fibre that comprises a plurality of fibres is proximally illuminated at the same time as the individual fibre during the calibration. Advantageously, by actuating different elements of the wavefront modulator the illumination system can be used particularly simply for calibration by means of simultaneous or temporally successive illumination of a plurality of individual fibres.

According to a further embodiment of the system according to the invention system, the illumination system may also comprise at least two illumination sources, at least one freely selectable individual fibre of the fibre bundle being illuminated by means of at least one first illumination source used in order to calibrate the fibre-optical system, and the entire bundle of optical fibres being illuminated by means of a second illumination source used in order to detect the object. In this embodiment, use can advantageously be made of the overall intensity of the illumination source used for calibration.

For example a laser is used as the illumination source.

In a further embodiment of the fibre-optical system according to the invention, a wavefront modulator comprising a plurality of individually actuatable elements is arranged in the optical path between the proximal facets of the optical fibres of the bundle and the illumination system, the elements of the wavefront modulator being able to be actuated by the signal processing platform in such a way that the inverse of the disturbance generated by the transmission by means of the bundle of optical fibres is impressed on the undisturbed light emitted by the illumination system for illuminating the object, by means of reflection at the elements of the wavefront modulator.

According to a variant of this embodiment of the fibre-optical system according to the invention, a light pattern, i.e. a spatial intensity and/or phase and/or polarisation state distribution, that can be freely adjusted over a wide parameter range is generated on the distal side of the bundle of optical fibres by means of the individually actuatable elements of the wavefront modulator. In particular, the light pattern may comprise a plurality of focal points.

This advantageously makes it possible to carry out scans using the fibre-optical system, to obtain depth information relating to an observed object, and to use the fibre-optical system in the manner of an actuator, e.g. for optical tweezers or radiation therapy.

According to a further variant of this embodiment of the fibre-optical system according to the invention, the wavefront modulator is a digital local spatial light modulator. Local spatial light modulators generally comprise an arrangement of LCoS or LCD cells or micromirrors on a semiconductor chip, which cells or mirrors can be individually actuated and tilted and/or lowered, as well as an application-specific integrated circuit. In this case, the spatial light modulator comprises at least one element, i.e. one micromirror, per fibre of the fibre bundle; a ratio of approximately 100 elements per fibre is conventional. The tilting or lowering of the individual micromirrors can advantageously be changed very quickly, such that it is possible to react instantly to changes in the system function.

Embodiments of the fibre-optical system according to the invention are characterised in that the means for partial reflection of the light emitted by the illumination system comprise a reflective surface, the reflectance of which is a function of the wavelength or of the polarisation state, or in that the reflective surface is semitransparent.

In an embodiment of the fibre-optical system according to the invention, the means for partial reflection of the light emitted by the illumination system comprise a reflective surface, the reflectance of which is a function of the wavelength of the light, such that the reflective surface functions as a wavelength-selective beam splitter. Within the meaning of the invention, the wavelength-selective reflective surface is used for reflecting a significant amount of light of a specific wavelength or of a wavelength range, and for transmitting a significant amount of light of another specific wavelength or of an other wavelength range. An in particular multi-layer reflective surface that functions in this manner is also referred to as a "dichroic filter". The advantage of this embodiment is in particular the fact that, when using light of two different wavelengths, in particular having a small wavelength difference, one wavelength selected as being slightly smaller and one wavelength as being slightly greater than the edge of the filter, calibration of the fibre-optical system and disturbance-corrected observation of an object can be carried out simultaneously (in a manner similar to wavelength division multiplexing). As a result, the object is illuminated and measured using light of at least one wavelength that is largely transmitted, and at the same time the fibre-optical system is calibrated using light of at least one wavelength that is largely reflected.

Correction can be carried out, by means of a known dispersion relation, even in the case of speckle decorrelation between the different wavelengths.

In an embodiment of the fibre-optical system according to the invention, the means for partial reflection of the light emitted by the illumination system comprise a reflective surface, the reflectivity of which is a function of the polarisation state of the light, such that the reflective surface functions as a polarisation state-dependent beam splitter (also referred to as a polarising beam splitter), a polarisation state of the light (e.g. right circular polarisation) is largely reflected and another polarisation state (e.g. left circular polarisation) is largely transmitted. As a result, the object is illuminated and measured using light of a polarisation state that is largely transmitted, and at the same time the fibre-optical system is calibrated using light of a polarisation state that is largely reflected. In the case of the preferred embodiment described, the calibration of the fibre-optical system and the disturbance-corrected observation of an object can advantageously be carried out simultaneously. A prerequisite therefor is that the fibres of the fibre bundle should be polarisation-maintaining; for example, fibre bundles comprising photonic-crystal fibres may be used.

In an embodiment of the fibre-optical system according to the invention, the means for partial reflection of the light emitted by the illumination system comprise a semitransparent mirror, the property "semitransparent" also comprising configurations of the mirror in which the light is not reflected or transmitted in equal fractions. The light can preferably be largely transmitted by the semitransparent mirror. Particularly preferably, only a fraction of the light intensity in the single-digit percent range is reflected by the semitransparent mirror and used for calibrating the fibre-optical system, and the remaining fraction is transmitted and used for observing the object. In this embodiment, the fractions used for calibration and the fractions used for disturbance-corrected observation of an object can be separated depending on the transit time of the light signal.

The means for partial reflection of the light are spaced apart from the distal facets of the fibre bundle. In particular, for example in the above-mentioned embodiments, the means are not directly and immediately deposited onto the distal facets of the fibre bundle. A spacing can be achieved for example by means of a glass spacer, to the distal end of which a reflective surface is applied. An analogous effect is achieved by the silica glass fibres of a fibre bundle, the core of which is Ge-doped in order to increase the refraction index, comprising an undoped region at the distal end, on which a reflective surface is deposited. The axial extent of the undoped region then specifies the spacing between the distal facets of the fibre bundle and the means for partial reflection of the light.

In a further embodiment of the fibre-optical system according to the invention, the means for detection comprise a CCD camera or a CMOS camera. In this case, the cameras used comprise at least one pixel per fibre of the fibre bundle; a ratio of from 10 to 100 pixels per fibre is conventional.

In a further embodiment of the fibre-optical system according to the invention, the signal processing platform comprises an FPGA (field programmable gate array) or a graphics processing unit (in particular using GPGPU=general-purpose computing on graphics processing units) or both. These components of the digital control system are advantageously characterised by low latency periods.

Features and details of the system, described according to the invention, of course also apply in connection with the method according to the invention, and vice versa.

The invention can be used for example in fibre-optical systems that are intended for imaging an object, e.g. endoscopes or microscopes. However, the invention can also be used in fibre-optical systems that are intended e.g. for laser-guided surgery, for cell stimulation, or optogenetic simulation. Applications in additive manufacturing are also possible. Of course, this list can reproduce only some of the many possible applications of the invention.

The invention is not limited to the embodiments shown and described, but instead comprises all embodiments that function in the same manner within the meaning of the invention. In order to implement the invention, it is a also expedient to combine the above-described variants and embodiments according to the invention, and individual features of the claims, with one another. The invention is not limited to the combinations of features specifically described, but can instead also be defined by any other possible combination of specific features of all the individual features disclosed overall, provided that the individual features are not mutually exclusive, or that a specific combination of individual features is not explicitly excluded.

The invention will be explained in the following with reference to embodiments, but without being restricted thereto.

DETAILED DESCRIPTION

Figure 1:
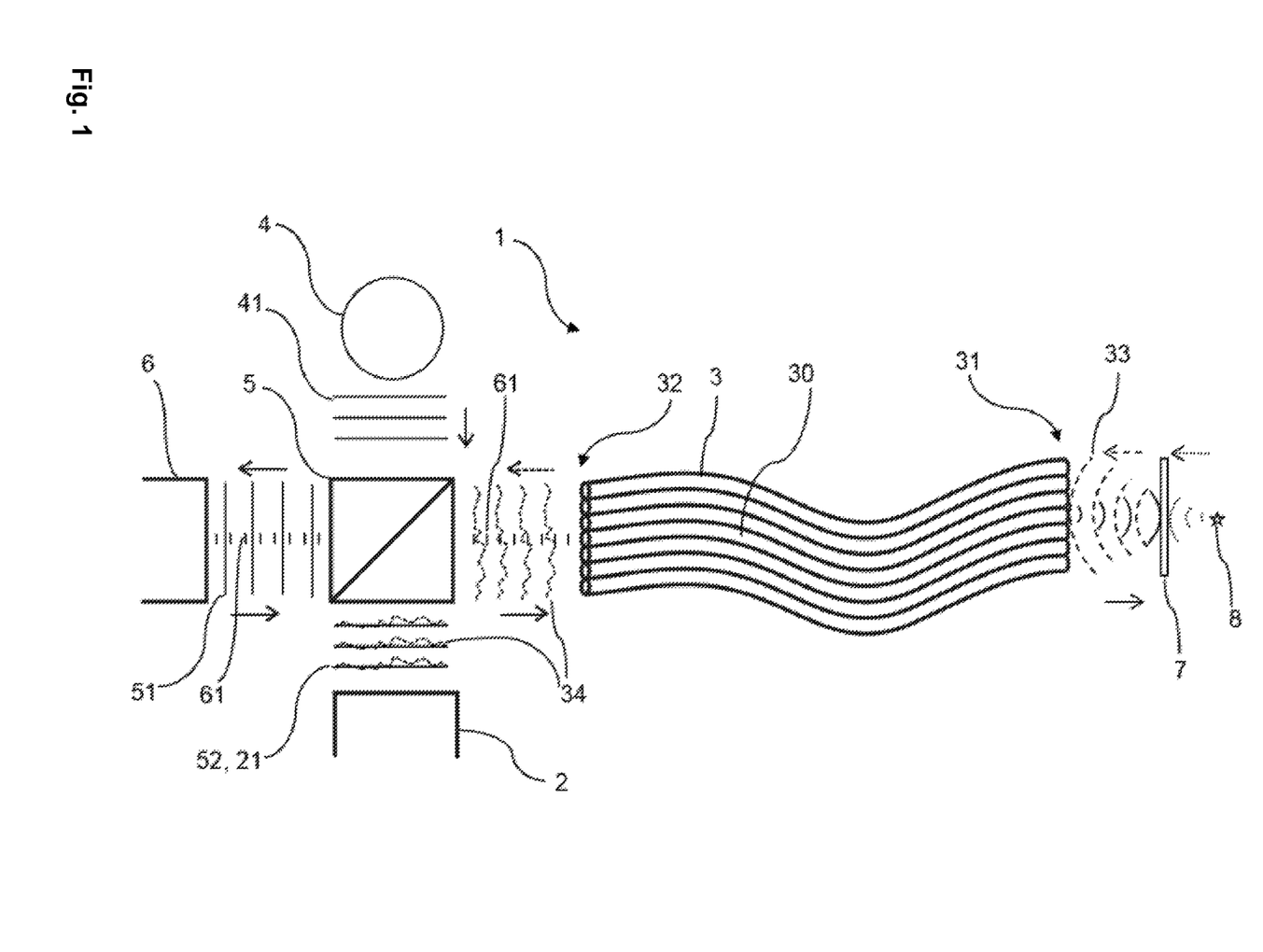
FIG. 1 shows a schematic diagram for determining the system function of a fibre bundle, the detector being arranged on the proximal side of the fibre bundle.

FIG. 1 shows a schematic diagram of a fibre-optical system 1 comprising a detector 2 on the proximal side 32 of the flexible fibre bundle 3, which diagram is intended to illustrate the calibration in the form of the initial measurement of the system function of the fibre bundle 3. In the embodiment, the phase information of the light that is subjected to distortion by being transmitted by means of the fibre bundle 3 is determined by means of digital holography.

The illumination system comprises an illumination source 4 and a spatial light modulator 6. Light emitted by the illumination source 4, which light is represented by the planar wavefronts 41, is divided, in a beam splitter 5, into a fraction 51 that is reflected towards the spatial light modulator 6, and a second fraction 52. The second fraction 52 is transmitted by the beam splitter 5 directly to the detector 2, and functions as a reference wave 21 for the holography.

The individual elements of the spatial light modulator 6 are tilted such that, of the fraction 51 of the illumination light, only a fraction 61 is reflected towards the fibre bundle 3 in the form of planar waves, by means of which exactly one individual fibre 30 of the fibre bundle 3 is illuminated proximally. On the distal side 31, the individual fibre 30 can be interpreted as the starting point of an elementary wave 33 that leaves the approximately punctiform individual fibre 30 and is reflected back, at least in fractions, towards the fibre bundle 30 by a means for partial reflection in the form of a semitransparent mirror 7. This corresponds, in optical terms, to illuminating the fibre bundle from the distal side 31 by means of a guide star 8 which constitutes the virtual image, resulting behind the semitransparent mirror 7, of the approximately punctiform individual fibre 30. Ultimately, therefore, at least a region of the fibre bundle 3 around the individual fibre 30 is illuminated distally by the elementary wave 33. The size of the region of the fibre bundle 3 that is distally illuminated in this manner is dependent on the spacing between the distal facet of the individual fibre 30 and the semitransparent mirror 7. FIG. 1 shows an embodiment in which the entire fibre bundle 3 is illuminated distally.

Wavefronts 34 distorted by the single phase difference $\Delta\phi$, by being transmitted by means of the fibre bundle 3, leave the fibre bundle 3 at the proximal end 32. Said wavefronts are reflected on the detector 2, which may be a CCD camera for example, at least in fractions, by means of the beam splitter 5, and the reference wave 21 is superposed thereon, such that the detector 2 records an interference pattern, by means of the digital evaluation of which in the signal processing platform (not shown) the phase information of the distorted waves 34 can be directly holographically extracted. The system function that represents the transmission properties of the fibre bundle 3 can thus be determined in the form of a transfer matrix.

Figure 2:
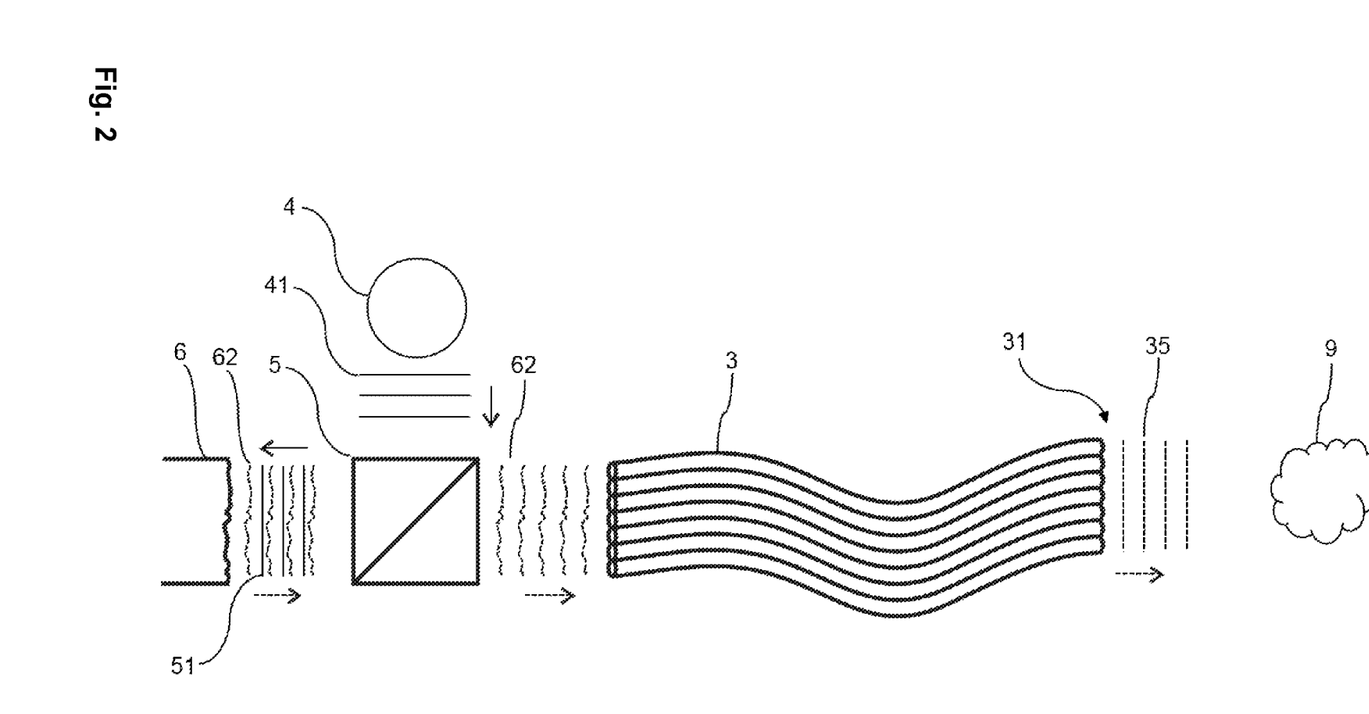
FIG. 2 shows a schematic diagram for compensating the system function of the fibre bundle before illuminating the object.

FIG. 2 shows a schematic diagram for compensating the system function that represents the transmission properties of the fibre bundle 3, by means of a spatial light modulator 6, before illuminating an object 9. According to the invention, the compensation of the system function is in each case preceded by the measurement and evaluation of said system function by means of a signal processing platform (not shown), an embodiment for calibrating the fibre bundle 3 being described in FIG. 1. The signal processing platform inverts the measured system function and adjusts the individual elements of the spatial light modulator 6 such that the inverse of the phase distortion caused by the fibre bundle 3 is impressed, by means of reflection at the spatial light modulator 6, on the light emitted by the illumination source 4, which light is again represented by planar waves 41 in this case and is reflected, at least in fractions, on the spatial light modulator 6 by means of the beam splitter 5. After reflection at the spatial light modulator 6, the wavefronts 62 have a distortion that is compensated during the subsequent transmission by means of the fibre bundle 3. Planar, disturbance-corrected waves 35 emerge from the fibre bundle at the distal end 31, which waves can be used for deflection-limited illumination of an object 9. The means for partial reflection that are arranged in front of the object 9 are not shown for reasons of clarity.

The individual elements of the spatial light modulator 6 can also be positioned such that the phase distortion experienced by the planar waves 51 due to the fibre bundle 3 is compensated. In addition, the positioning of the individual elements of the spatial light modulator 6 is such that, when the light emerges distally from the fibre bundle 3, focussing of the light results in one focal point or a plurality of focal points (not shown). When the planar waves 51 are reflected at the spatial light modulator 6, the inverted system function is thus impressed thereon, and focussing takes place. The pre-deformed and focussed wavefronts (not shown) are then guided into the fibre bundle 3, where the phase distortion is compensated while the focussing is maintained. Focussed, disturbance-corrected, undistorted waves leave the fibre bundle 3 distally.

The invention claimed is:

1. A method for illuminating and detecting an object by light, comprising at least the following method steps:
    a) calibrating a coherent bundle of optical fibres, comprising
        i) proximal illumination of at least one freely selectable individual fibre of the coherent bundle of optical fibres with light;
        ii) reflecting the light at least in part at means for partial reflection of the light that are spaced apart from distal facets of the optical fibres of the bundle, such that a region of the bundle of optical fibres that comprises more than one individual fibre is illuminated distally by the reflected light, wherein the reflected light corresponds to the light emanating from a virtual image of the illuminated individual fibres;
        iii) detecting the spatial intensity distribution of the reflected light subjected to disturbance by being transmitted by the distally illuminated region of the bundle of optical fibres, or a spatial intensity distribution of an interference pattern generated by coherent superposing a reference wave on the reflected light subjected to disturbance by being transmitted by the distally illuminated region of the bundle of optical fibres;
        iv) evaluating detected data at least in order to directly extract a single phase difference ΔΦ of the reflected light subjected to disturbance by being transmitted by the distally illuminated region of the bundle of optical fibres;
        v) determining a system function that mirrors transmission properties of the distally illuminated region of the bundle of optical fibres;
        vi) repeating sub-method steps i) to v) to determine a system function that mirrors transmission properties of the entire bundle of optical fibres;
    b) disturbance-corrected proximal illumination of the entire bundle of optical fibres by light, and detection of the object arranged in the optical path after the means for partial reflection, or
        disturbance-corrected detection of the object arranged in the optical path after the means for partial reflection following uncorrected proximal illumination of the entire bundle of optical fibres by means of light,
        wherein the disturbance correction of the illumination is carried out in that the inverse of the system function is impressed on the light emitted by an illumination system, by means of interaction with a wavefront modulator comprising individually actuatable elements, such that, following transfer through the bundle of optical fibres, a wave field that largely corresponds to that emitted by the illumination system is available for proximal illumination of an object arranged in the optical path after the means for partial reflection;
        wherein the disturbance correction of the detection is carried out in that the spatial intensity distribution of the light subjected to disturbance by being transmitted by the bundle of optical fibres, following interaction with the object, or the spatial intensity distribution of an interference pattern generated by coherently superposing a reference wave on the light subjected to disturbance by being transmitted by the bundle of optical fibres, following interaction with the object, is numerically corrected by means of applying the inverse system function.

2. The method according to claim 1, wherein, in sub-method step i), at least two non-adjacent individual fibres of the bundle of optical fibres are proximally illuminated at the same time, at least two virtual images of the individual fibres resulting in sub-method step ii), by which images of non-overlapping regions of the bundle of optical fibres are illuminated distally.

3. The method according to claim 1, wherein, in sub-method step i), at least one freely selectable individual fibre is illuminated proximally by at least one first illumination source, and in method step b) the disturbance-corrected or uncorrected proximal illumination of the entire coherent bundle of optical fibres is carried out by a second illumination source or,
    in sub-method step i) the proximal illumination of at least one freely selectable individual fibre and in method step b) the disturbance-corrected or uncorrected proximal illumination of the entire bundle of optical fibres are carried out using exactly one illumination source, the light interacting with a wavefront modulator that is arranged in the optical path between the illumination source and the coherent bundle of optical fibres, at least for the purpose of proximal illumination of at least one freely selectable individual fibre.

4. The method according to claim 1, wherein the means for partial reflection largely reflect or largely transmit the light on the distal side of the bundle of optical fibres, depending on the wavelength thereof.

5. The method according to claim 1, wherein the means for partial reflection largely reflect or largely transmit the light on the distal side of the bundle of optical fibres, depending on a polarisation state thereof.

6. The method according to claim 1, wherein the evaluation of the detected data and the extraction at least of the phase information of the reflected light subjected to disturbance by being transmitted by the bundle of optical fibres is carried out by digital holography from the spatial intensity distribution of an interference pattern generated by coherently superposing a reference wave on the reflected light that is subjected to disturbance by being transmitted by the bundle of optical fibres.

7. The method according to claim 1, wherein the evaluation of the detected data and the extraction, from the spatial intensity distribution, at least of the phase information of the reflected light subjected to disturbance by being transmitted by the bundle of optical fibres is carried out by numerical reconstruction, by a phase retrieval method.

8. The method according to claim 1, wherein a freely adjustable light pattern is generated on the distal side of the bundle of optical fibres.

9. A fibre-optical system for illuminating and detecting an object by light, comprising
   a coherent bundle of optical fibres;
   an illumination system for proximally illuminating the coherent bundle of optical fibres;
   means for partial reflection of the light, which means are arranged in the optical path of the light emitted by the illumination system, between distal facets of the optical fibres of the bundle and the object at a spacing from the distal facets;
   means for detecting the spatial intensity distribution of the light subjected to disturbance by being transmitted by the bundle of optical fibres, or the spatial intensity distribution of an interference pattern generated by coherently superposing a reference wave on the light subjected to disturbance by being transmitted by the bundle of optical fibres;
   a signal processing platform at least for evaluating detected data and for determining at least phase information of the light that is subjected to disturbance by being transmitted by the bundle of optical fibres;
   wherein the illumination system is adapted to illuminate at least one freely selectable individual fibre of the bundle of optical fibres in order to calibrate the bundle of optical fibres, and to illuminate the entire bundle of optical fibres in order to observe the object.

10. The fibre-optical system according to claim 9, wherein the illumination system comprises at least one illumination source and a wavefront modulator that comprises a plurality of individually actuatable elements, the wavefront modulator being arranged in the optical path between proximal facets of the optical fibres of the bundle and the at least one illumination source, the elements of the wavefront modulator being oriented such that, in order to calibrate the bundle of optical fibres, at least one freely selectable individual fibre of the bundle of optical fibres is illuminated by the at least one illumination source.

11. The fibre-optical system according to claim 9, wherein the illumination system comprises at least two illumination sources, at least one freely selectable individual fibre of the bundle of optical fibres being illuminated by at least one first illumination source in order to calibrate the bundle of optical fibres, and the entire bundle of optical fibres being illuminated by a second illumination source in order to observe the object.

12. The fibre-optical system according to claim 9, wherein a wavefront modulator comprising a plurality of individually actuatable elements is arranged in an optical path between proximal facets of the optical fibres of the bundle and the illumination system, the elements of the wavefront modulator being able to be actuated by the signal processing platform in such a way that an inverse of the disturbance generated by the transmission by means of the bundle of optical fibres is impressed on the undisturbed light emitted by the illumination system for illuminating and detecting the object, by reflection at the elements of the wavefront modulator.

13. The fibre-optical system according to claim 12, wherein an adjustable light pattern is generated on a distal side of the bundle of optical fibres by the individually actuatable elements of the wavefront modulator.

14. The fibre-optical system according to claim 12, wherein the wavefront modulator is a digital local spatial light modulator.

15. The fibre-optical system according to claim 9, wherein the means for partial reflection of the light comprise a reflective surface that functions as a wavelength-dependent beam splitter.

16. The fibre-optical system according to claim 9, wherein the means for partial reflection of the light comprise a reflective surface that functions as a polarisation state-dependent beam splitter.

17. The fibre-optical system according to claim 9, wherein the means for partial reflection of the light comprise a semi-transparent reflective surface.

18. The fibre-optical system according to claim 9, wherein the means for detection comprise a CCD camera or a CMOS camera.

19. The fibre-optical system according to claim 9, wherein the signal processing platform comprises an FPGA (field programmable gate array) or a graphics processing unit or both.

* * * * *